US 8,702,596 B2

(12) United States Patent
Kaye et al.

(10) Patent No.: US 8,702,596 B2
(45) Date of Patent: Apr. 22, 2014

(54) BIOPSY INLET VALVE IMPROVEMENTS

(75) Inventors: Christopher J. Kaye, Concord, OH (US); Gary E. Mann, Mentor, OH (US)

(73) Assignee: United States Endoscopy Group, Inc., Mentor, OH (US)

( * ) Notice: Subject to any disclaimer, the term of this patent is extended or adjusted under 35 U.S.C. 154(b) by 282 days.

(21) Appl. No.: 13/234,580

(22) Filed: Sep. 16, 2011

(65) Prior Publication Data

US 2012/0071713 A1 Mar. 22, 2012

Related U.S. Application Data

(60) Provisional application No. 61/383,777, filed on Sep. 17, 2010.

(51) Int. Cl.
| | | |
|---|---|---|
| A61B 1/00 | (2006.01) | |
| A61B 1/12 | (2006.01) | |
| A61M 5/14 | (2006.01) | |
| A61M 5/178 | (2006.01) | |
| A62B 9/02 | (2006.01) | |

(52) U.S. Cl.
USPC .......... 600/154; 600/159; 600/106; 604/256; 604/167.01; 604/167.02; 128/205.24

(58) Field of Classification Search
USPC ............... 600/154, 104, 159, 153, 156, 106; 604/256, 167.03, 167.01, 164.08, 604/167.02, 167.06, 6.1; 606/153, 46; 251/149.1; 128/205.24
See application file for complete search history.

(56) References Cited

U.S. PATENT DOCUMENTS

| | | | |
|---|---|---|---|
| 4,198,958 A | | 4/1980 | Utsugi |
| 4,240,411 A | | 12/1980 | Hosono |
| 4,412,531 A | | 11/1983 | Chikashige |
| 4,416,273 A | | 11/1983 | Grimes |
| 4,436,519 A | | 3/1984 | O'Neill |
| 4,572,163 A | | 2/1986 | Collins et al. |
| 4,649,904 A | | 3/1987 | Krauter et al. |
| 4,653,477 A | * | 3/1987 | Akui et al. .............. 600/154 |
| 4,715,360 A | * | 12/1987 | Akui et al. .............. 600/154 |
| 4,736,732 A | | 4/1988 | Shomonaka et al. |

(Continued)

FOREIGN PATENT DOCUMENTS

| | | |
|---|---|---|
| WO | 97/34650 A1 | 9/1997 |
| WO | 2007/120713 | 10/2007 |

OTHER PUBLICATIONS

International Search Report and Written Opinion from International Application No. PCT/US07/08947 dated Dec. 26, 2007.

*Primary Examiner* — John P Leubecker
*Assistant Examiner* — Ronald D Colque
(74) *Attorney, Agent, or Firm* — Calfee, Halter & Griswold LLP (57) ABSTRACT

A valve apparatus device provides surgical instruments with sealable access to an inlet port of an endoscope instrument channel. The valve has a hollow body with a distal end that releasably attaches to the inlet port, and a flexible diaphragm seal dividing the body into a proximal chamber and a distal chamber. An instrument opening extends through the diaphragm seal for the passage of instruments therethrough, and connects the chambers together. The diaphragm seal is configured to seal with a surgical instrument inserted into the instrument opening. At least one fluid transfer member is provided to fluidly interconnect the proximal chamber to the distal chamber when the surgical instrument is sealed within the instrument opening.

21 Claims, 6 Drawing Sheets

(56) References Cited

U.S. PATENT DOCUMENTS

| | | | | |
|---|---|---|---|---|
| 4,809,679 | A | 3/1989 | Shimonaka et al. | |
| 4,874,364 | A | 10/1989 | Morris et al. | |
| 5,209,219 | A | 5/1993 | Hollobaugh | |
| 5,234,417 | A | 8/1993 | Parks et al. | |
| 5,247,966 | A | 9/1993 | Stevens et al. | |
| 5,324,254 | A | 6/1994 | Phillips | |
| 5,382,242 | A | 1/1995 | Horton et al. | |
| 5,437,646 | A | 8/1995 | Hunt et al. | |
| 5,697,888 | A | 12/1997 | Kobayashi et al. | |
| 5,725,478 | A | 3/1998 | Saad | |
| 5,800,493 | A | 9/1998 | Stevens et al. | |
| 5,820,606 | A | 10/1998 | Davis et al. | |
| 5,863,286 | A | 1/1999 | Yabe et al. | |
| 5,891,014 | A | 4/1999 | Ariba | |
| 5,895,377 | A * | 4/1999 | Smith et al. | 604/256 |
| 5,971,917 | A | 10/1999 | Komi et al. | |
| 6,117,070 | A * | 9/2000 | Akiba | 600/154 |
| 6,126,592 | A | 10/2000 | Proch et al. | |
| 6,126,633 | A | 10/2000 | Kaji et al. | |
| 6,142,981 | A | 11/2000 | Heck et al. | |
| 6,159,182 | A * | 12/2000 | Davis et al. | 604/167.06 |
| 6,165,124 | A * | 12/2000 | Ouchi | 600/154 |
| 6,254,529 | B1 * | 7/2001 | Ouchi | 600/154 |
| 6,258,065 | B1 * | 7/2001 | Dennis et al. | 604/167.03 |
| 6,383,132 | B1 | 5/2002 | Wimmer | |
| 6,569,087 | B2 | 5/2003 | Naito et al. | |
| 6,663,598 | B1 | 12/2003 | Carrillo, Jr. et al. | |
| 6,666,818 | B2 | 12/2003 | Shindsa | |
| 6,808,521 | B1 | 10/2004 | McMichael | |
| 6,860,869 | B2 | 3/2005 | Dennis | |
| 6,863,661 | B2 | 3/2005 | Carrillo, Jr. et al. | |
| 7,025,721 | B2 | 4/2006 | Cohen et al. | |
| 7,112,185 | B2 | 9/2006 | Hart et al. | |
| 7,220,226 | B2 | 5/2007 | Rovegno | |
| 7,226,411 | B2 * | 6/2007 | Akiba | 600/154 |
| 7,537,583 | B2 | 5/2009 | Carrillo, Jr. et al. | |
| 7,645,266 | B2 | 1/2010 | Carrillo, Jr. et al. | |
| 7,670,285 | B2 * | 3/2010 | Yamaya | 600/154 |
| 7,717,878 | B2 | 5/2010 | Smith | |
| 7,967,744 | B2 | 6/2011 | Kaye et al. | |
| 8,172,806 | B2 * | 5/2012 | Smith | 604/167.01 |
| 8,357,123 | B2 * | 1/2013 | Gresham | 604/167.02 |
| 8,454,563 | B2 * | 6/2013 | Insignares et al. | 604/167.03 |
| 2003/0069549 | A1 | 4/2003 | MacMahon et al. | |
| 2003/0195472 | A1 * | 10/2003 | Green et al. | 604/167.04 |
| 2004/0167379 | A1 | 8/2004 | Akiba | |
| 2004/0171990 | A1 * | 9/2004 | Dennis et al. | 604/167.03 |
| 2005/0027165 | A1 | 2/2005 | Rovegno | |
| 2005/0059934 | A1 * | 3/2005 | Wenchell et al. | 604/167.01 |
| 2005/0171402 | A1 | 8/2005 | Cohen et al. | |
| 2005/0267417 | A1 | 12/2005 | Secrest et al. | |
| 2006/0041232 | A1 * | 2/2006 | Stearns et al. | 604/167.06 |
| 2006/0047284 | A1 * | 3/2006 | Gresham | 606/108 |
| 2006/0135850 | A1 | 6/2006 | Cohen et al. | |
| 2006/0149305 | A1 * | 7/2006 | Cuevas et al. | 606/191 |
| 2006/0229565 | A1 * | 10/2006 | Dennis et al. | 604/167.03 |
| 2006/0235356 | A1 * | 10/2006 | Yamaya | 604/256 |
| 2006/0253077 | A1 * | 11/2006 | Smith | 604/167.06 |
| 2006/0287578 | A1 | 12/2006 | Hamazaki | |
| 2007/0282168 | A1 | 12/2007 | Kaye et al. | |
| 2008/0033363 | A1 * | 2/2008 | Haberland et al. | 604/167.03 |
| 2009/0149813 | A1 * | 6/2009 | Franer et al. | 604/167.06 |
| 2009/0234293 | A1 * | 9/2009 | Albrecht et al. | 604/167.02 |
| 2009/0270685 | A1 * | 10/2009 | Moreno et al. | 600/203 |
| 2009/0270817 | A1 * | 10/2009 | Moreno et al. | 604/264 |
| 2010/0004507 | A1 | 1/2010 | Kaye | |
| 2010/0004599 | A1 * | 1/2010 | Zhou et al. | 604/167.04 |
| 2010/0022958 | A1 * | 1/2010 | Moreno et al. | 604/165.02 |
| 2010/0240956 | A1 | 9/2010 | Secrest | |
| 2010/0256567 | A1 * | 10/2010 | Smith | 604/167.03 |
| 2011/0046449 | A1 * | 2/2011 | Minnelli et al. | 600/205 |
| 2011/0087170 | A1 * | 4/2011 | Insignares | 604/167.03 |
| 2011/0152625 | A1 * | 6/2011 | Smith | 600/208 |
| 2011/0288483 | A1 * | 11/2011 | Zhou et al. | 604/167.03 |

\* cited by examiner

BIOPSY INLET VALVE IMPROVEMENTS

CROSS REFERENCE TO RELATED APPLICATIONS

The present application hereby claims the benefit of the provisional patent application of the same title, Ser. No. 61/383,777 filed on Sep. 17, 2010, the disclosure of which is hereby incorporated by reference in its entirety with the exception of formerly filed paragraphs [003]-[005].

FIELD OF THE APPARATUS

The present apparatus relates, in general, to valves and to a biopsy inlet valve for use with the instrument channel inlet port of an endoscope

BACKGROUND

Endoscopes are well-known in the art and are commonly used for numerous medical procedures that involve intubation of the esophagus and gastro-intestinal tract. As such, many devices and accessory instruments have been developed that relate to the operation of an endoscope. One such device well-known in the endoscopic art field is commonly referred to as a biopsy valve.

A biopsy valve attaches to the instrument channel inlet port of an endoscope, and provides sealable access thereto. In the beginning of an exemplary endoscopic procedure, the biopsy valve is attached to the inlet of the accessory instrument channel to close off the channel, and the endoscope is then inserted into a body cavity or lumen of a patient. The body cavity or lumen is then insufflated by the endoscope to improve visualization and to provide a working space therein. In doing so, a positive pressure is created in the body and in the channel. The pressure is retained or held back by use of the attached biopsy valve. At least one opening within the biopsy valve is configured to expand and grip and seal around the accessory instrument shaft when instruments are inserted into the biopsy valve, and to squeegee liquids from the outer surface of the instrument as it is withdrawn. The at least one opening is configured to close when the instrument is removed to prevent insufflation loss.

BRIEF SUMMARY

The apparatus overcomes the above-noted and other deficiencies of the prior art by providing a valve that provides a surgical instrument with sealed access to an inlet port of an endoscope instrument channel. The valve comprises a hollow tubular body having a distal end of the hollow configured to removably attach to the inlet port. A proximal end of the hollow is sealed with a removable cap. An internal wall separates the hollow into a proximal chamber and a distal chamber. A sealable instrument opening has a first portion extending through the cap, and a second portion extending through the wall for surgical instrument access to the inlet port through the valve. And, an interconnection member provides fluid communication between the proximal and distal chambers when the surgical instrument is sealed within the sealable instrument opening extending through the internal wall.

In one aspect of the apparatus, a valve provides a surgical instrument with sealed access to an inlet port of an endoscope instrument channel. The valve comprises a hollow tubular body with a distal end of the hollow configured to removably attach to the inlet port. A flexible diaphragm having an instrument opening extending therethrough is positioned within the hollow to separate the hollow into a proximal chamber and a distal chamber that communicate through the instrument opening. The instrument opening is further configured to seal against the surgical instrument when the instrument is inserted therein. And, a pressure transfer member is configured to equalize pressure between the proximal and distal chambers when the instrument opening is sealed against the surgical instrument.

In yet another aspect of the apparatus, a valve provides a surgical instrument with sealable access to an inlet port of an endoscope instrument channel. The valve comprises a hollow tubular body having a distal end of the hollow configured to removably attach to the inlet port. A flexible seal separates the hollow into a proximal chamber and a distal chamber, the flexible seal also having an instrument seal opening extending therethrough between the proximal and said distal chambers. At least one orifice connects the proximal chamber to the distal chamber. Wherein when at least one of the surgical instruments accesses the inlet port of the endoscope instrument channel through the valve, and the surgical instruments seals with the instrument seal opening, the at least one orifice provides fluid communication between said proximal and distal chambers.

These and other objects and advantages of the present apparatus shall be made apparent from the accompanying drawings and the description thereof.

BRIEF DESCRIPTION OF THE FIGURES

The accompanying drawings, which are incorporated in and constitute a part of this specification, illustrate embodiments of the improved biopsy valve apparatus, and, together with the general description of the improved biopsy valve given above, and the detailed description of the embodiments given below, serve to explain the principles of the present improved biopsy valve apparatus.

DETAILED DESCRIPTION

The following description of certain examples of the apparatus should not be used to limit the scope of the present apparatus. Other examples, features, aspects, embodiments, and advantages of the apparatus will become apparent to those skilled in the art from the following description, which is by way of illustration, one of the best modes contemplated for carrying out the apparatus. As will be realized, the apparatus is capable of other different and obvious aspects, all without departing from the spirit of the apparatus. Accordingly, the drawings and descriptions should be regarded as illustrative in nature and not restrictive. Indeed, the invention as described by the claims is broader than and unlimited by the preferred embodiments, and the terms in the claims have their full ordinary meaning.

Figure 1:
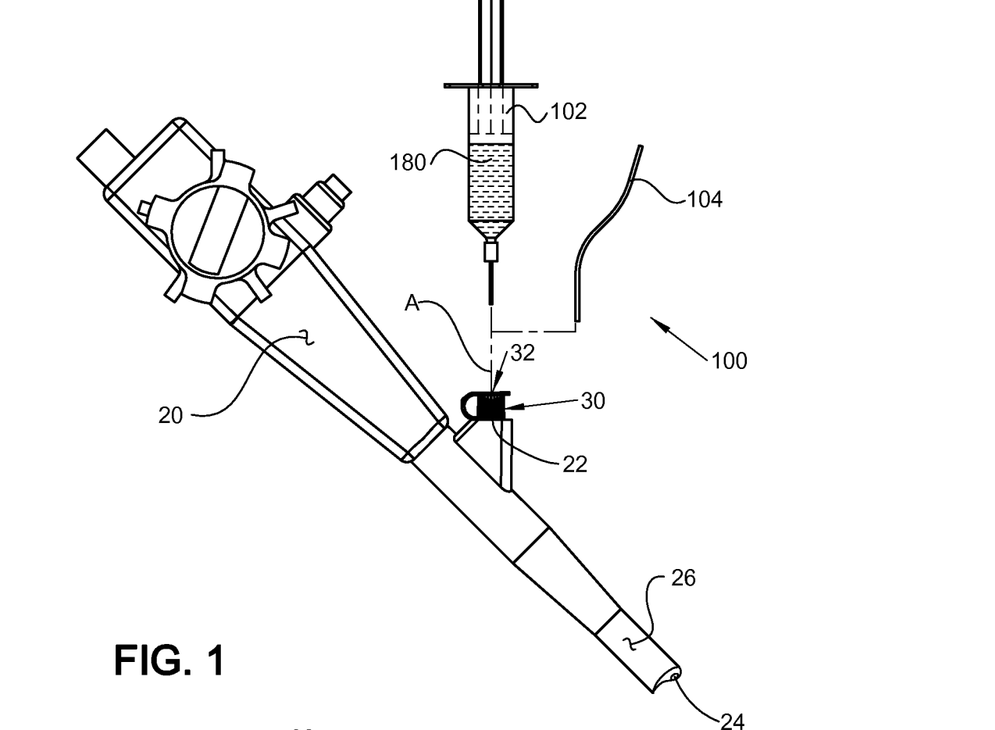
FIG. 1 is a side view of an improved biopsy inlet valve shown attached to an instrument port of an endoscope, with a cap of the biopsy valve in a closed position, and with a syringe and a surgical instrument poised for insertion into the biopsy valve.

FIG. 1 is a side view showing a biopsy valve 30 of the present apparatus attached onto an instrument inlet port 22 of a partially cross sectioned endoscope 20. Biopsy valve 30 provides access to the instrument inlet port 22 through a sealed instrument passage 32 extending through valve 30 along an axis "A" to provide passage to the sealed instrument passage 32. The inlet port 22 operably connects to an instrument channel 24 that extends through the endoscope 20 from the inlet port 22 to the surgical site. One or more surgical instruments 100 can access the surgical site through the biopsy valve 30 by being inserted into the inlet port 22 and into the instrument channel 24. Other surgical instruments 100 such as a medical device 104 or a saline filled syringe 102 can be inserted into the instrument passage 32 for tasks such tissue resection or washing the instrument channel 24, respectively. Multiple instruments 100 such as a guide wire and a cannula can be simultaneously inserted into the improved biopsy valve 30.

The valve 30 is highly adaptable for use to seal off the inlet port 22, and to allow access by an instrument 100, or for irrigation of the endoscope instrument channel. It should be understood by those with ordinary skill in the art that a wide variety of endoscopic instruments 100 can be used in the practice of the present apparatus, such as for example, snares, retrieval nets or forceps. It should also be understood by those with ordinary skill in the art that a wide variety of irrigation sources can be used in the practice of the present invention, such as for example liquid filled syringes, electrical fluid pump devices, and manual or foot actuated liquid pump devices.

Figure 2:
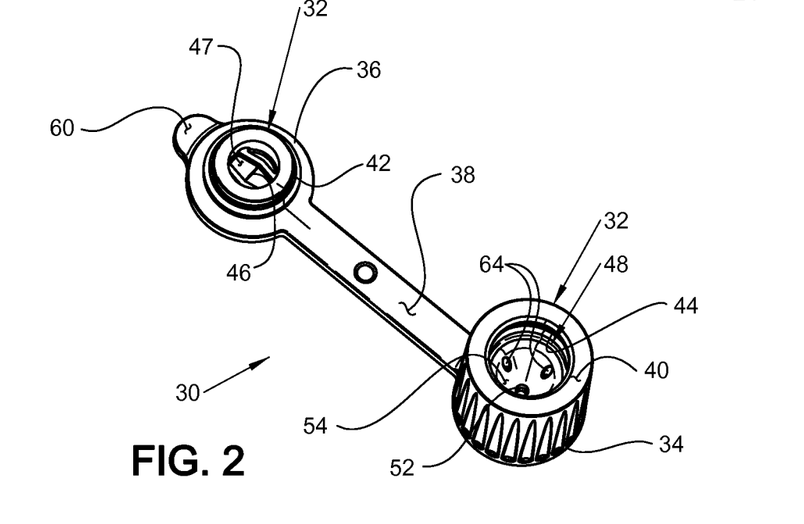
FIG. 2 is an isometric view of a proximal side of the valve of FIG. 1 with the cap shown in an open position.
Figure 3:
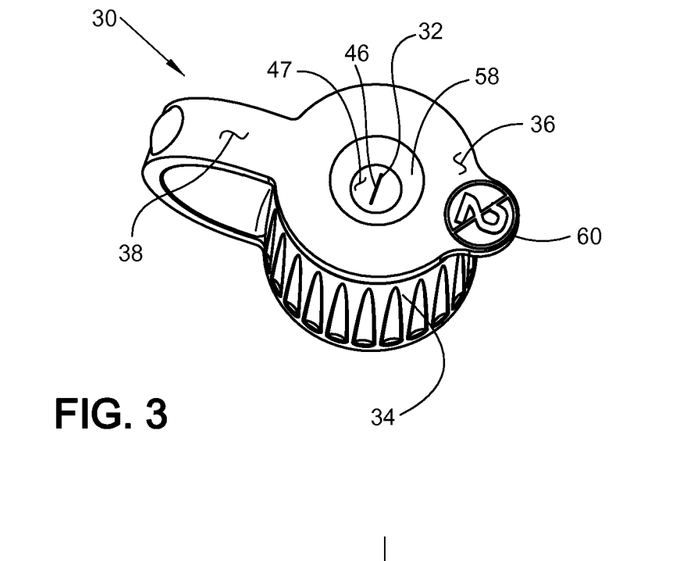
FIG. 3 is an isometric view of a proximal end of the closed valve of FIG. 1.
Figure 4:
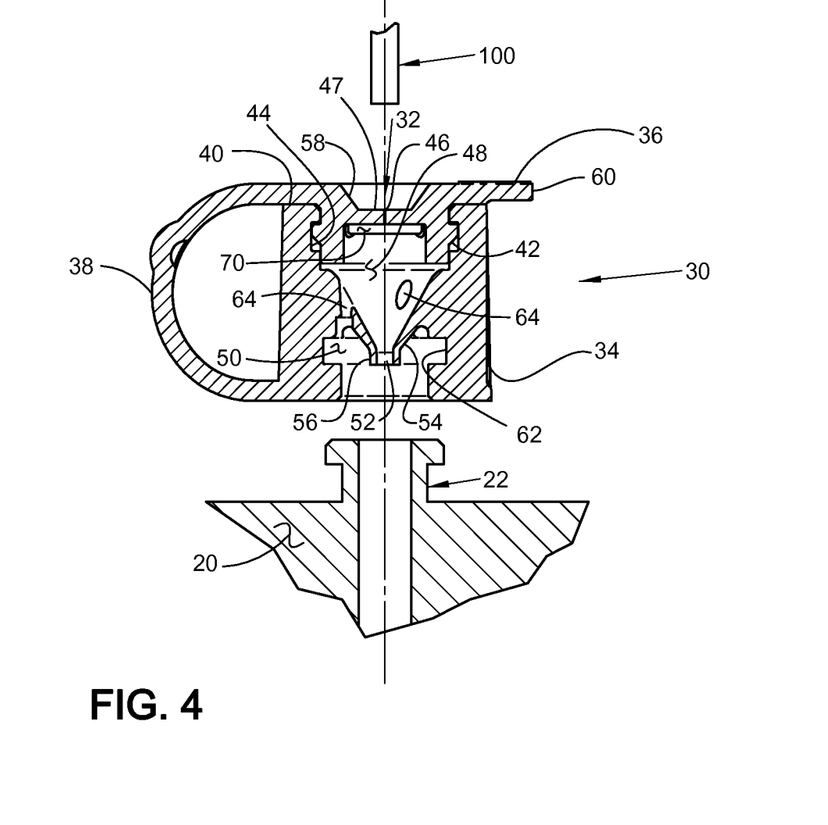
FIG. 4 is a cross-sectional side view of the closed valve poised above an inlet port of the endoscope with a surgical instrument poised above the valve.

FIGS. 1-4 show the biopsy valve 30 of the present apparatus. Biopsy valve 30 comprises a generally cylindrical body 34 connected to a flip cap 36 by a strap 38. Flip cap 36 can be in an open position shown in FIG. 2, or can removably seal to the body 34 in a closed position as shown in FIGS. 1, 3, and 4. Body 34, flip cap 36, and strap 38 can be integrally molded, or assembled from a plurality of parts, and can be formed from one or more materials. These materials can include but are not limited to one or more of a rubber or an elastomeric material such as a thermoplastic elastomer (TPE), flexible plastic, rigid plastics, rigid materials such as metals, rubbers, or combinations thereof. As shown in FIG. 3, closed flip cap 36 is configured to removably seal against a proximal end 40 (FIG. 2) of the body 34, and is held in this closed position by the locking engagement of the flip cap 36 with the body 34. The biopsy valve 30 can be used with the flip cap 36 in the open or closed position, and can seal with small and larger shaft sizes of the instrument 100. Instrument passage 32 extends through the valve 30 in the open or the closed cap position, and provides passage for instruments therethrough. Instrument passage 32 extends through body 34 when the flip cap 36 is open, and extends through both flip cap 36 and body 34 when the flip cap 36 is closed.

Turning to FIG. 2, the valve 30 is shown in an open position and a self closing slit 46 can be seen extending through an elastomeric floor 47 of the flip cap 36. The slit 46 moves into position to align with the instrument passage 32 when the flip cap 36 is moved into the closed position. Slit 46 permits the insertion of various devices 100 into the cap 36 and further into the instrument passage 32, such as for example, a guidewire, needles, and irrigation tubes. Slit 46 creates a pressure tight seal with the instruments 100. Body 34 can include a diaphragm seal 54 that defines a hollow of the valve as a proximal chamber 48 recessed below the proximal end 40 of the body 34 and as a distal chamber 50 (FIG. 4) below the diaphragm seal 54. Proximal chamber 48 may include a circular body slot 44 configured to lock with a circular cap rib 42 extending from cap 36. Diaphragm seal 54 can define a floor for the proximal chamber 48, and a recessed ceiling for the distal chamber 50. The diaphragm seal 54 is flexible to receive instruments therethrough, and in embodiments, can be uniformly spaced about a longitudinal axis extending through the biopsy valve.

Figure 11:
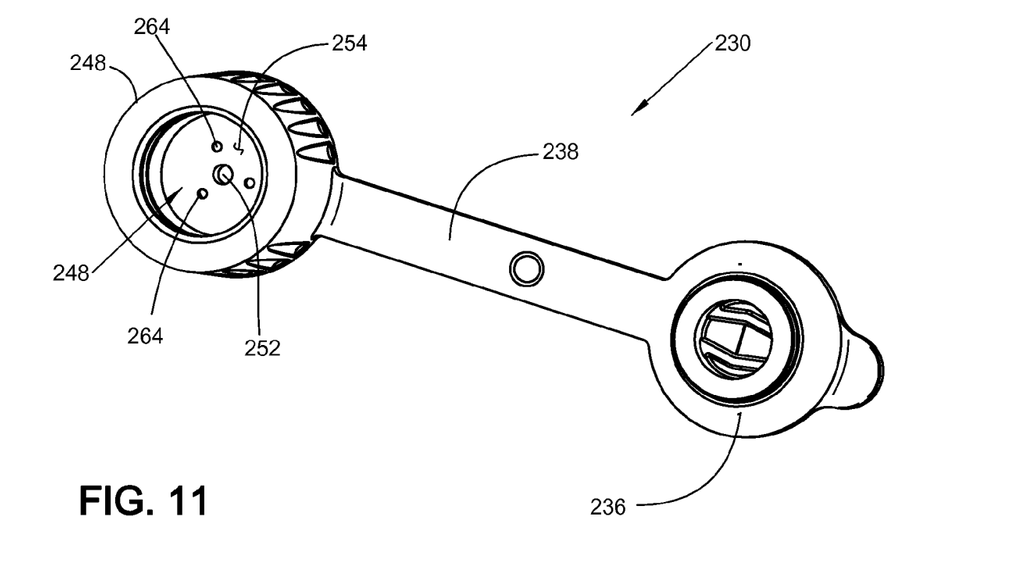
FIG. 11 is an isometric proximal view of an alternate embodiment of a valve having a flat diaphragm seal.
Figure 12:
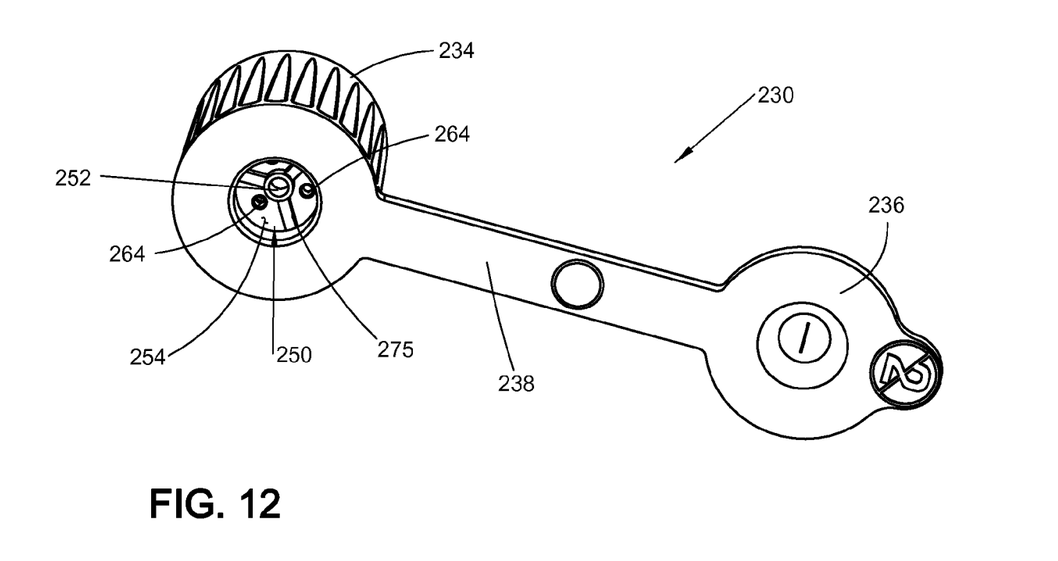
FIG. 12 is an isometric distal view of the valve of FIG. 11.

Whereas the diaphragm seal 54 in FIG. 2 is shown as a conical diaphragm, the diaphragm seal 54 of the present apparatus is not limited thereto but can be any other shape such as, for example, a flat diaphragm 254 as shown in FIGS. 11 and 12 which will be discussed later. In FIG. 2, an instrument opening 52 extends centrally through the distal most portion of the conical diaphragm seal 54 to communicate with the distal chamber 50 located below the conical diaphragm seal 54 (FIG. 4). When the flip cap 36 is open, large diameter inserted instruments 100 can pass through instrument opening 52 to seal against the conical diaphragm seal 54, or when the flip cap 36 is closed, can seal with both diaphragm seal 54 and the self closing slit 46 in the flip cap 36. Closing the flip cap 36 allows smaller diameter instruments to seal with the slit 36 rather than with the instrument opening 52 of diaphragm seal 54. The conical diaphragm seal 54 and the self closing slit 46 within the floor 47 can be constructed from an elastomeric or flexible material that is normally biased to a home position shown in FIG. 4, and can return to the position of FIG. 4 after a deflection. For example, if a distal or proximal force is applied to the conical diaphragm seal 54, the seal 54 can move distal or proximal from the normal conical position in response to the force. Once the biasing force is removed, the conical diaphragm seal 54 will return to the normal position unless blocked.

At least one orifice 64 or member can be provided to connect the proximal chamber 48 to the distal chamber 50 to provide fluid communication therebetween. A fluid 280 can be a gas 80, an incompressible liquid 180, or a combination thereof, and can include body fluids such as blood, mucous, small particles of solids or semi-solids, and the like. In the exemplary embodiment shown in FIGS. 2, 4, 5, 9, and 10, the at least one orifice 64 can extend through the conical diaphragm seal 54 to interconnect the proximal and distal chambers 48, 50, and to transfer fluids between chambers 48, 50 in response to movement of the conical diaphragm seal 54.

At least one orifice 64 or member is not limited to the design shown in FIGS. 2, 4, 5, 9, and 10. In another alternate exemplary embodiment of the orifice 64, the orifice can extend through the body 34 rather than the seal 54 to connect the proximal and distal chambers 48, 50 (not shown). In yet another alternate embodiment, orifice 64 can extend through a pipe or other connection member that communicates between the proximal and distal chambers, 48, 50 (not shown). Alternately, the exemplary orifice 64 can extend through the body 34, or connect chambers 48, 50 together in any other manner through any other part or features. The number of orifices 64 extending through the conical diaphragm seal 54 can vary, and can be more than one. The orifice 64 can be placed in any orientation and spacing as long as there is at least one. The at least one orifice 64 can be any size or shape, and can include at least one arcuate portion, a straight portion or an irregular portion thereof. For example, all or part of orifice 64 can be round, oval, square, triangular, hexagonal, arcuate, regular, irregular, a slit, or any other shape. The orifice 64 can be uniform or non-uniform along a length thereof and the sides of orifice 64 can be smooth, irregular, stepped, tapered, or arcuate. Orifice 64 can have an axis (not shown) extending between the proximal and distal ends of the orifice 64, and the axis of the orifice 64 can be straight, skewed, curved, spiraled, stepped and the like along the length thereof, and the axis can be parallel or non-parallel to the longitudinal axis of body 34. Orifice 64 can remain normally open such as a fixed diameter hole, or can open and close like a valve. An exemplary orifice 64 that functions as a valve is well within in the spirit of the apparatus, and examples thereof can comprise but are not limited to a slit cut into the conical diaphragm seal 54 to act as a pressure valve, or a duck billed valve (not shown) that is recessed into or protrudes from the diaphragm seal 54. The orifice 64 of the present apparatus can be any size or shape, and in an exemplary embodiment thereof, orifice 64 can be circular with a diameter between about 0.006 inches to about 0.10 inches. Alternately, in another exemplary embodiment, circular orifice 64 can have a diameter between about 0.010 inches to about 0.040 inches. And in yet another exemplary embodiment, circular orifice 64 has a diameter between about 0.020 inches to about 0.030 inches.

As shown in at least FIG. 2, at least one orifice 64 can be three orifices equally spaced around the conical diaphragm seal 54 and in FIG. 2, two of the three exemplary orifices can be seen. A step can be placed within the sectioned orifice 64 as shown in at least FIGS. 4 and 5. One exemplary use of the at least one orifice 64 is to equalize fluid pressure between the proximal chamber 48 and distal chamber 50. It is of note that when the valve 30 is on the endoscope 20, the at least one orifice 64 can equalize pressure between the proximal and the distal chambers 48, 50 when the cap 36 is open (FIG. 2) or closed (FIG. 3). The advantages of the at least one orifice 64 will be discussed in greater detail below.

As best shown in FIG. 3, the floor 47 is recessed into a top of the flip cap 36 and is surrounded by a tapered guide surface 58. The taper of the guide surface 58 assists the operator during surgery by guiding surgical instrument 100 into the center of the flip cap 36, and into the slit 46 of the instrument opening 52. A grip tab 60 extends from the flip cap 36 and is configured to be grasped between an operators thumb and index finger. Pulling on the grip tab 60 releases flip cap 36 from cylindrical body 34 and moves the flip cap to the open position of FIG. 2.

FIG. 4 is a cross section of a biopsy valve 30 with the flip cap 36 closed. The biopsy valve is shown moving down towards the inlet port 22 of the endoscope 20 to attach thereto. A surgical instrument 100 is poised to enter the instrument passage 32 of the biopsy valve 30 once valve 30 is releasably secured onto the inlet port 22. As shown in FIG. 4, when the flip cap 36 is closed, instrument passage 32 comprises the slit 46 extending through flip cap 36, a proximal chamber 48 in body 34, the distal chamber 50 in body 34, and the instrument opening 52 connecting proximal chamber 48 to distal chambers 50. In the cross sectional view, it can be seen that the conical diaphragm seal 54 further comprises a ring seal 56 that extends distally into proximal chamber 48 with circular instrument opening 52 extending therethrough. Ring seal 56 provides greater sealing area, increased tear resistance, and is configured to seal with surgical instruments 100 having a circular diameter about equal to or larger than the opening 52. Ring seal 56 is designed to allow instrument 100 to slip therethrough while maintaining a seal therewith, but in certain conditions, the ring seal 56 can grip the shaft of an instrument 100 tightly before slipping and can move the conical diaphragm seal 54 in the direction of movement of the instrument 100.

In FIG. 4, the conical diaphragm seal 54 can be seen separating a hollow bore of the body 34 into a proximal chamber 48 and a distal chamber 50. Distal chamber 50 can further comprise at least one attachment member 62 such as a groove configured to releasably secure the biopsy valve 30 to the instrument inlet port 22. At least one orifice 64 can be seen extending longitudinally through conical diaphragm seal 54 to interconnect the proximal and distal chambers 48, 50. The exemplary at least one orifice 64 will be discussed in greater detail below.

Figure 5:
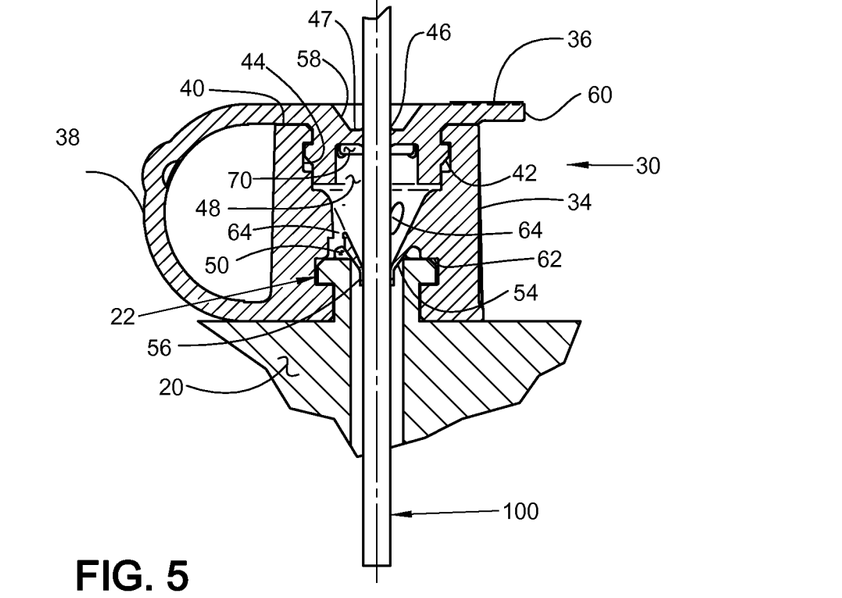
FIG. 5 is a cross-sectional side view showing the closed valve installed on the inlet port of the endoscope with the surgical instrument extending through the valve and into the endoscope.

FIG. 5 shows the biopsy valve 30 releasably attached to the inlet port 22 of the endoscope 20 to create a seal therewith. Surgical instrument 100 is shown inserted into the biopsy valve 30, and into the inlet port 22 of the endoscope 20. The instrument inlet port 22 is shown received into the distal chamber 50 of the body 34 where the attachment feature 62 is releasably gripping the instrument inlet port 22. The insertion of surgical instrument 100 creates a pressure tight seal with the self closing slit 46 of the instrument passage 32. The surgical instrument 100 extends downward through proximal chamber 48 of the body 34, through the circular instrument opening 52 in conical diaphragm seal 54, and into the proximal distal chamber 50. Ring seal 56 grips and seals with the shaft of surgical instrument 100 as it passes through the instrument opening 52. Both ring seal 56 and slit 46 are configured to squeegee the shaft of the surgical instrument 100. The exemplary at least one orifice 64 is shown connecting proximal chamber 48 with distal chamber 50 even when instrument 100 is inserted as shown.

Figure 6:
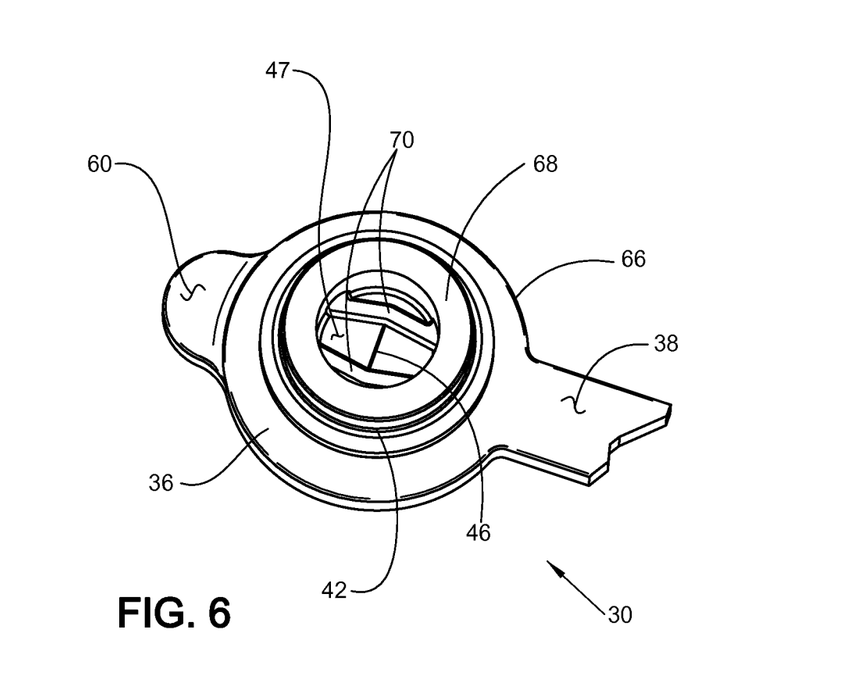
FIG. 6 is an enlarged isometric view of the open cap shown in FIG. 2.

FIG. 6 shows an enlarged view of a distal side of the flip cap 36 to illustrate an exemplary feature thereof. Flip cap 36 is connected to flexible strap 38. In FIG. 6, a cylindrical cap ring 68 extends upwards from flip cap 36 with cap rib 42 extending radially in a ring outward therefrom. A distal side of the recessed floor 47 can be seen surrounded by cap ring 68 with slit 46 centrally located therein. A pair of reinforcement members 70 flank slit 46 with each end of slit 46 adjacent to a member 70. Reinforcement members 70 provide two exemplary functions. First, reinforcement members 70 are placed adjacent to each end of the slit 46 to reduce the risk of a crack or tear propagating across the floor 47 from an instrument insertion. When an instrument 100 is inserted therein, the slit 46 expands and creates high stress concentrations at each end of the slit 46. The reinforcement members 70 advantageously provide extra material at the highly stressed ends of the slit 46, and the extra material spreads out the high stress concentrations. Thus, reinforcement members 70 dilute higher stress values to lower stress values and reduce the chances of tearing the slit 46. Reinforcement members 70 can also be extended across the floor 47 to have a second exemplary function in that they stiffen the recessed floor 47. Stiffening the floor 47 with stiffeners (aka reinforcement members 70) reduces up and down oil canning deflections of the floor 47 from a surgical instrument 100 being pushed into or pulled from the slit 46, and helps ensure that the two surfaces on either side of the slit 46 return to the same plane as the remainder of the floor 47 to reduce a potential leak path.

Figure 7:
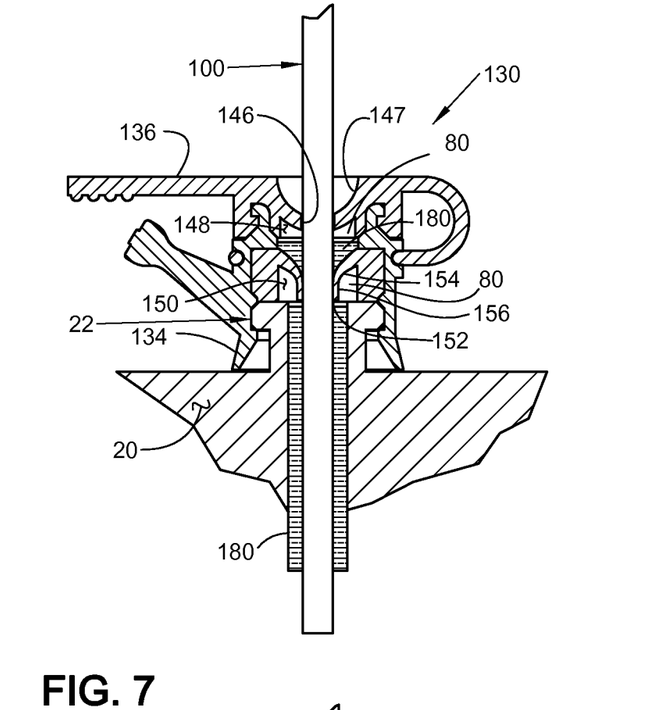
FIG. 7 is a cross-sectional side view of a prior art valve attached to an endoscope showing a non-moving surgical instrument inserted through the valve and into the endoscope, and showing fluids within the prior art valve and endoscope.
Figure 8:
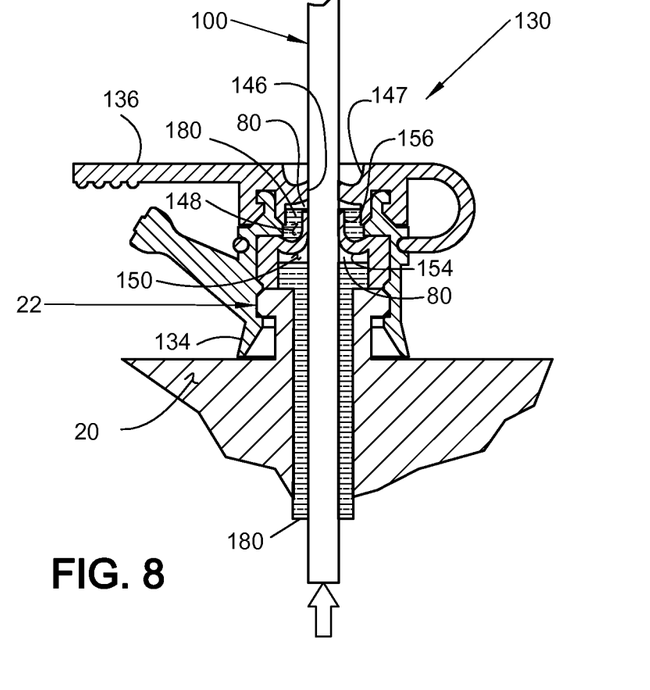
FIG. 8 is a cross-sectional view of the prior art valve of FIG. 7 showing the surgical instrument moving upwards to evert a diaphragm seal of the valve, and showing fluids drawn upwards by the everted diaphragm seal.

FIGS. 7 and 8 show a prior art biopsy valve 130 attached to the instrument inlet port 22 of an endoscope 20 during a surgery. At the beginning of a surgery, some surgeons place a small amount of saline or fluid at the entrance of the valve to "wet" the instrument shaft as it passes through the valve. The wetted shaft lubricates the seal as it passes, and reduces the force required to insert or withdraw the instrument. Fluids can be carried through a seal with a moving wet shaft. During a surgery, the physician's view of the internal work site can be clouded by blood, mucous, or fecal matter necessitating removal of an inserted instrument, and a cleansing application of a water spray down the instrument channel of the scope. When an instrument is re-inserted into the channel, the cleansing water spray or various body fluids can ooze from the surgical work site into a narrow gap between an exterior of the instrument and the instrument channel via capillary action. These fluids can then be pushed towards the biopsy valve by internal insufflation pressures, or by being carried along into the endoscope 20 by a withdrawing instrument shaft. Additionally, if the biopsy valve has a diaphragm seal 154, the flexible diaphragm seal 154 can a pumping action can be created by an outward "oil can" movement of the flexible diaphragm. In some cases, the diaphragm seal 154 can evert outward as shown in FIG. 8. It is believed that when the everted diaphragm seal 154 is released by the withdrawn instrument, the diaphragm 154 may snap inward towards the original "at rest" position of FIG. 7. The snap return movement of the diaphragm seal 154 may impact or push on the pooled fluids 80, 180 within, and create higher fluid pressure at biopsy valve seals 147, 154.

FIGS. 7 and 8 show the behavior of a prior art biopsy valve 130 during use, particularly in the control of a gas 80 and a liquid 180. Prior art biopsy valve 130 is intended to be exemplary in nature and is not limited to the depicted shape or configuration shown. The prior art biopsy valve 130 comprises a prior body 134 with a removable cap 136. A prior proximal chamber 148 and a prior distal chamber 150 are separated by a prior diaphragm seal 154 within body 134. A prior opening 152 extends through a center of the prior diaphragm seal 154 and a prior annular seal 156 can be formed with or around opening 152. In FIGS. 7 and 8, opening 152 is show sealed around an instrument 100 inserted through prior art biopsy valve 130 and into inlet port 22 of endoscope 20. Once the instrument 100 forms a seal with prior diaphragm seal 154, the prior proximal chamber 148 and a prior distal chamber 150 are separate chambers that cannot communicate. Pressure differentials can be created therebetween as the instrument 100 moves in and out of endoscope 20 in response to surgeon manipulation. This motion deflects the prior diaphragm seal 154 of the prior art biopsy valve 130. The prior diaphragm seal 154 is constructed at least in part from an elastomeric material, is normally biased to the position shown in FIG. 7, and will return to the normal position after deflection. A prior slit 146 extends through a prior floor 147 of the removable cap 136 and slit 146 is shown held open by the shaft of instrument 100. The prior floor 147 is also constructed at least in part from an elastomeric material and has a normally cupped position shown in FIG. 7. when the shaft of instrument 100 is at rest. In FIG. 8 the shaft is moving upwards. Liquids 180 are shown pooled within the inlet port 22 and in the biopsy valve 130 and all spaces within the prior art biopsy valve 130 that are not filled with liquids 180 are filled with gas 80.

During the course of the surgery shown in FIGS. 7 and 8, various surgical instruments 100 have been inserted and removed through the prior art biopsy valve 130, and several saline washes have been applied to rinse the instrument channel 24 of the endoscope. As shown in FIG. 7, the saline and body fluids within the patient and endoscope have formed the liquid 180 which has migrated during surgery from the up and down movement of the instrument 100 to create a pool within the inlet port 22 and within the prior art biopsy valve 130. This upwards migration can be caused by insufflation pressure within the patient, and by upward movement of the instrument shaft. A pool of liquid 180 has risen to be within the prior distal chamber 140 and is just below contact with a distal portion of a diaphragm seal 154 of the prior art device biopsy seal 130. A small amount of liquid 180 has puddled within the proximal chamber 148 from movement of a wet instrument shaft 100. The liquid 180 is trapped within the proximal chamber 148 until the instrument 100 is removed, at which point the liquid 180 can drain into the pool of liquid 180 below through a central prior opening 152 in diaphragm seal 154.

In FIG. 8, the surgeon is rapidly removing the surgical instrument 100 from the endoscope 20 and the prior art biopsy valve 130, and the rapid upward movement has drawn more liquid 180 along with the shaft of instrument 100 and into the distal chamber 150. The rapid withdrawing motion of surgical instrument 100 has also everted the conically shaped diaphragm seal 154 and bowed the prior floor 147 upward as shown. The everted diaphragm seal 154 has decreased the volume of the sealed proximal chamber 148, increased the pressure therein, and moved the liquids 80 trapped within closer to the upward bowing prior slit 146.

The upward movement and eversion of prior diaphragm seal 154 can create a suction to convert the seal 154 into a diaphragm pump that can draw additional liquid 180 upward. In FIG. 6 the normal at rest position of the diaphragm seal 154 is shown as an upside down cone (dashed outline), and the new everted position of diaphragm seal 154 is a right side up cone. A double conic volume of liquid 180 equal to the difference between those two conical positions can be sucked upwards towards or into the prior biopsy valve 130.

In FIG. 8, the shaft of instrument 100 is moving upward and is nearly ready to be released from the cylindrical prior annual seal 156. When the instrument shaft 100 moves upwards an amount sufficient to disengage from the everted diaphragm seal 154, the everted diaphragm seal 154 is free to revert back to the normal non-everted cone shape of FIG. 5. As the diaphragm seal 154 snaps or returns to the normal position, pressure is applied onto the liquid 180 captured within the distal chamber, and the liquid 180 water flows or jets into the proximal chamber 148 through the central prior opening 152 within the diaphragm seal 154 (not shown). As the shaft of instrument 100 exits the prior slit 146 of the removable cap 136, the upwardly bowed prior floor 147 snaps back to the normal horizontal position shown in FIG. 5 (not shown).

Figure 9:
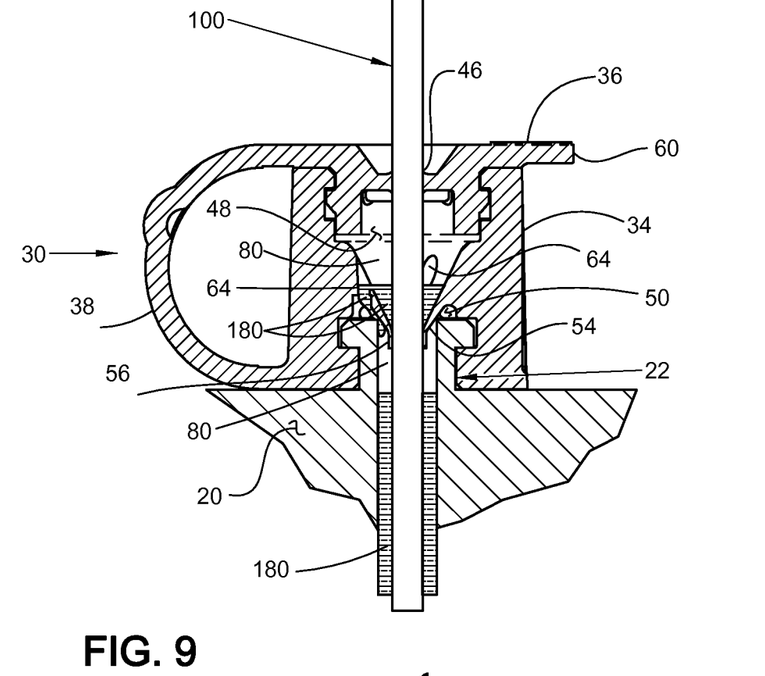
FIG. 9 is a cross-sectional side view of the valve and endoscope of FIG. 1 showing a non-moving surgical instrument inserted therein and showing fluids draining down towards the endoscope, the fluids moving from a distal chamber to a proximal chamber of the valve through one or more an orifices connecting the chambers.
Figure 10:
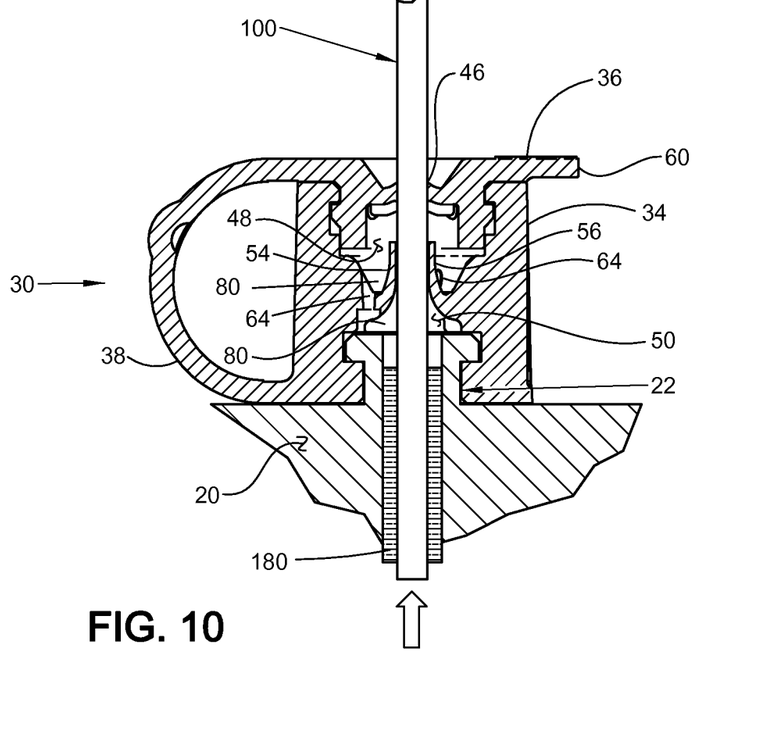
FIG. 10 is a cross-sectional side view of the valve of FIG. 9 showing an upwards moving surgical instrument everting the diaphragm seal which drained the fluids from the upper chamber into the lower chamber to maintain a constant pressure between the proximal and distal chambers of the valve.

FIGS. 9 and 10 show how the present biopsy valve 130 with at least one orifice 66 offers unexpected fluid handling improvements over the prior art designs. In FIG. 9, the improved biopsy valve 30 is shown attached to the inlet port 22 of the endoscope 20 with the surgical instrument 100 inserted therein to access a surgical site through an instrument channel 24 of endoscope 20. During the surgery, liquid 180 comprising saline and body fluids have migrated to pool in the inlet port 22 below the improved biopsy valve 130. The liquid 180 has migrated to that position from a combination of surgical site insufflation pressure, and from fluids carried along with movement of the shaft of instrument 100 within the endoscope 20. Liquid 180 has been carried into the proximal chamber 48 by the movement of the wet shaft of the instrument 100 and has pooled in the conical diaphragm seal 54. The liquid 180 has risen in the conical diaphragm seal 54 until the liquid 180 reaches a bottom edge of one or more orifices 64. Once that occurs, any additional liquid 180 within the cone will flow downward through orifices 64, into the distal chamber 50, and into the inlet port 22. In FIG. 9, the excess liquid 180 is shown flowing down the leftmost orifice 64 and is moving from the proximal chamber 48 and into the distal chamber 50. Should the instrument 100 move upward, conical diaphragm seal 54 will deflect upwards into the proximal chamber 48, pressurize the upper or proximal chamber 48, and force fluids 180 and/or gas 80 into the orifice 64 and into the distal chamber 50 until chamber pressures match. Should the conical diaphragm seal 54 of this description move downward into the distal chamber 50, gas 80 will migrate into proximal chamber 48 to equalize pressures. Thus, at least one orifice 64 can act as a pressure control valve or member to equalize pressure differentials between the proximal and distal chambers 48, 50, and provide passage of fluids such as liquids 180 and/or gas 80 therebetween.

FIG. 10 shows the instrument 100 being rapidly withdrawn from the improved biopsy valve 30. Conical diaphragm seal 54 has moved upwards into the proximal chamber 48 to increase the pressure therein, forcing liquids 80 to drain into the distal chamber 50 and then into inlet port 22. In this view, the proximal and distal chambers 48, 50 are equally pressurized with gas 80. It is of note that unlike the prior art device, the placement of orifices 64 into the conical diaphragm seal 54 convert the upwardly moving and everting conical diaphragm seal from a diaphragm pump to a chamber pressure equalizer. Once the instrument 100 moves out of the instrument opening 52, the conical diaphragm seal 54 snaps or moves from the everted position of FIG. 10 to the normal conical shape of FIG. 9 and gas 80 shifts from the distal chamber 50 to the proximal chamber 48 through orifices 64 and instrument opening 52 until pressures are equal. The reader is advised to note that liquids 80 are not involved in this process and have been moved away from the moving conical diaphragm seal 54 by the inclusion of orifices 64 therein.

An additional advantage of the improved biopsy valve 30 is that the orifices 64 have been observed to work as drains. For example, when the improved biopsy valve 30 is placed on an endoscope 20 with the flip cap 36 open, the addition of liquid 180 around an inserted instrument 100 was observed to drain into the orifices 64 and not towards the operator.

Likewise, an additional advantage of the improved biopsy valve 30 was observed when suction was applied to the endoscope 20 with a surgical instrument 100 inserted therein. While suction is primarily directed to a distal end of the endoscope 20 to enhance the procedure being performed, if the cap 36 of the valve 30 is open, the suction can create a negative pressure on the instrument channel 24 and on the at least one orifice 64, and can suck fluids back down the channel 24 and away from the user.

Another advantage of the improved biopsy valve 30 is that the area of the openings extending through the conical diaphragm seal 54 is increased beyond the instrument opening 52 by the addition of the orifices 64. With prior art designs, the area of the openings through the biopsy valve 130 is limited by the diameter or area of the prior opening 152 extending through a center of the prior diaphragm seal 154. With the improved biopsy valve 30, the increased area of the openings results in higher volume of fluid flow through the improved biopsy valve 30, and provides improved pressure washing of the endoscope 20.

Another alternate exemplary embodiment of the present apparatus is shown in FIGS. 10 and 11 where biopsy valve 230 has a flat diaphragm seal 254. The flat diaphragm seal 254 separates the biopsy valve 230 into an interior proximal chamber 248 (FIG. 11) and a distal chamber 250 (FIG. 12). A central instrument opening 252 extends through flat diaphragm seal 254 for passage of an instrument therethrough. At least one orifice 264 extends through flat diaphragm seal 254 to equalize fluid pressure interior proximal chamber 248 and distal chamber 250 when an instrument is sealed within central instrument opening 252. This pressure equalization process via one or more orifices 264 is described above. Biopsy valve 230 also comprises a body 248, a flip cap 236, and a strap 238 extending therebetween. A slit 266 extends through flip cap 236 for instrument passage and sealing. FIG. 12 shows a bottom view of the biopsy valve 230 to show the flat diaphragm seal 254 forming a ceiling of the distal chamber 250.

An optional embodiment of ribs 275 can be added to the flat diaphragm seal 254 for additional stiffness. Rib members 275 can reduce proximal and distal deflection of the flat diaphragm seal 254. Stiffener members 275 are not limited to ribs, but can be any shape or member that reduces deflection of the diaphragm seal 254. Ribs 275 are shown on the distal side of the diaphragm seal 254, but can be formed or attached to either side thereof. Stiffener members 275 can be used singly or in combination with the orifices 64, and in exemplary embodiments, can comprise one or more ribs attached to a conical (not shown) or flat diaphragm seal 254 (FIG. 12). The ribs, or stiffener members 275, can extend radially outward along the diaphragm seal 254 from a ring seal 256 towards the body 234.

Alternately, in other embodiments, the flat diaphragm seal 254 can be domed, rectangular, pyramidal or any other shape.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While the present improved biopsy valve apparatus has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, the body 30 can be formed all or in part from a non-elastomeric material such as a rigid plastic, a deformable plastic, or a generally rigid plastic molded in sufficient thinness to act as a flexible plastic.

What is claimed is:

1. A valve for providing a surgical instrument with sealable access to an inlet port of an endoscope instrument channel, said valve comprising:
   a hollow tubular body having a distal end of said hollow configured to removably attach to the inlet port, and a proximal end of said hollow sealed with a removable cap;
   an internal wall separating said hollow into a proximal chamber and a distal chamber;
   a sealable instrument opening having a first portion extending through said cap and a second portion extending through said wall for surgical instrument access to the inlet port through said valve; and
   an interconnection member providing fluid communication between said proximal and distal chambers when the surgical instrument is sealed within said portion of sealable instrument opening extending through said internal wall.

2. The valve of claim 1 wherein at least a portion of said internal wall is deflectable proximally and distally.

3. The valve of claim 2 wherein said internal wall is a flat disk.

4. The valve of claim 2 wherein said internal wall is a tapered cone.

5. The valve of claim 1 wherein said portion of said sealable instrument opening extending through said cap is a slit.

6. The valve of claim 5 wherein said portion of said sealable instrument opening extending through said cap further comprises at least one reinforcement member adjacent to an end said slit, said at least one reinforcement member configured to reduce crack propagation from said end of said slit.

7. The valve of claim 1 wherein said cap further comprises at least one stiffening member extending across at least a portion of said cap to reduce proximal and distal distortion of said sealable instrument opening therein.

8. The valve of claim 1 wherein said internal wall further comprises a ring seal around said opening.

9. The valve of claim 1 wherein said wall further comprises at least one stiffening rib thereon to reduce deflection of said internal wall.

10. The valve of claim 1 wherein at least a portion of said valve is formed from an elastomeric material.

11. A valve for providing a surgical instrument with sealable access to an inlet port of an endoscope instrument channel, said valve comprising:
    a hollow tubular body with a distal end of said hollow configured to removably attach to the inlet port;
    a flexible diaphragm having an instrument opening extending therethrough, said flexible diaphragm positioned within said hollow to separate said hollow into a proximal chamber and a distal chamber that communicate through said instrument opening, said instrument opening further configured to seal against the surgical instrument when the instrument is inserted therein; and
    a pressure transfer member configured to equalize pressure between said proximal and distal chambers when said instrument opening is sealed against the surgical instrument.

12. The valve of claim 11 further comprising a cap configured to close a proximal end of the hollow with a sealed cap opening extending therethrough, said cap opening providing a surgical instrument with sealable access to the inlet port of the endoscope through said instrument opening.

13. The valve of claim 12 wherein at least a portion of the cap is formed from an elastomeric material and the sealed cap opening is a slit therein.

14. The valve of claim 13 wherein said cap includes a floor with the sealed cap opening extending therethrough and said floor further comprises at least one floor stiffening member adjacent said sealed cap opening.

15. The valve of claim 11 wherein said pressure transfer member is a passage communicating between said proximal chambers and said distal chamber independent from said instrument opening.

16. The valve of claim 11 wherein at least a portion of the pressure transfer member is arcuate.

17. The valve of claim 11 wherein at least a portion of the pressure transfer member is straight.

18. A valve for providing a surgical instrument with sealable access to an inlet port of an endoscope instrument channel, said valve comprising:
    a hollow tubular body having a distal end of said hollow configured to removably attach to the inlet port;
    a flexible seal separating the hollow into a proximal chamber and a distal chamber, said flexible seal having an instrument seal opening extending therethrough between said proximal and said distal chambers;
    at least one orifice connecting to said proximal chamber and said distal chamber, wherein when the surgical instruments accesses the inlet port of the endoscope instrument channel through the valve and the surgical instruments seals with said instrument seal opening, said at least one orifice provides fluid communication between said proximal and distal chambers.

19. The valve of claim 18 wherein said at least one orifice connecting said proximal chamber and said distal chamber extends through said flexible seal.

20. The valve of claim 18 wherein said instrument seal opening is centrally located within said flexible seal, and said at least one orifice comprises three orifices equally spaced around said instrument seal opening between said hollow tubular body and said instrument seal opening.

21. The valve of claim 18 wherein the valve further comprises a flip cap removably attached to a proximal end of said hollow, said flip cap further configured with a sealable orifice for sealable instrument insertion therethrough to provide sealed access to the inlet port through said instrument seal opening.

* * * * *